United States Patent
Luo et al.

(10) Patent No.: US 8,820,145 B2
(45) Date of Patent: Sep. 2, 2014

(54) MEASURING DEVICE FOR MEASURING CONSISTENCY OF CEMENT SLURRY FOR A CONSISTOMETER

(75) Inventors: Yuwei Luo, Hebei (CN); Yutian Wang, Liaoning (CN); Zhenyu Yang, Hebei (CN); Shiwen Yu, Liaoning (CN); Weijun Lv, Hebei (CN); Qingshun Wang, Hebei (CN); Weihan Ling, Hebei (CN); Zhenlun Li, Liaoning (CN); Bin Han, Liaoning (CN)

(73) Assignees: China Oilfield Services Limited, Sanhe, Hebei (CN); Shenyang Jinouke Petroleum Instrument Technology Development Co., Ltd, Shenyang, Liaoning (CN)

( * ) Notice: Subject to any disclaimer, the term of this patent is extended or adjusted under 35 U.S.C. 154(b) by 351 days.

(21) Appl. No.: 13/164,822

(22) Filed: Jun. 21, 2011

(65) Prior Publication Data

US 2012/0024046 A1 Feb. 2, 2012

(30) Foreign Application Priority Data

Jul. 30, 2010 (CN) .......................... 2010 1 0242213

(51) Int. Cl.
*G01N 11/14* (2006.01)

(52) U.S. Cl.
CPC ..................................... *G01N 11/14* (2013.01)
USPC .......................................................... 73/54.31

(58) Field of Classification Search
None
See application file for complete search history.

(56) References Cited

U.S. PATENT DOCUMENTS

| | | | | |
|---|---|---|---|---|
| 1,930,629 A | * | 10/1933 | Stephens | 73/54.35 |
| 3,053,079 A | * | 9/1962 | Miller et al. | 73/54.31 |
| 4,466,276 A | * | 8/1984 | Ruyak et al. | 73/54.35 |
| 4,736,624 A | * | 4/1988 | Arnstein et al. | 73/54.35 |
| 4,823,594 A | * | 4/1989 | Gray | 73/54.01 |
| 7,287,416 B1 | * | 10/2007 | Bi | 73/54.28 |
| 7,412,877 B1 | * | 8/2008 | Bi | 73/54.28 |
| 8,156,798 B1 | * | 4/2012 | Bi | 73/149 |
| 8,230,723 B2 | * | 7/2012 | Moon et al. | 73/54.28 |
| 2010/0071442 A1 | * | 3/2010 | Moon et al. | 73/54.28 |

FOREIGN PATENT DOCUMENTS

CA 1223458 A * 6/1987

* cited by examiner

*Primary Examiner* — Hezron E Williams
*Assistant Examiner* — Nathaniel Kolb
(74) *Attorney, Agent, or Firm* — MacMillan, Sobanski & Todd, LLC

(57) ABSTRACT

This present invention relates to a measuring device for measuring consistency of cement slurry for a consistometer. The measuring device comprises a high-pressure vessel, a slurry cup and a magnetic driver, wherein the slurry cup is rotatably mounted inside the high-pressure vessel by the magnetic driver, stir blades are hanged in the slurry cup, and the magnetic driver is driven by a driving motor which is located outside the high-pressure vessel and is further provided with a tension sensor. The invention cancels the conventional mode for measuring consistency by a potentiometer, uses the tension sensor to measure the torque transferred from the driving motor to the magnetic driver, i.e. the cutting torque created by the stir blades on cement slurries within the slurry cup, thereby measuring the consistency of cement slurry.

14 Claims, 2 Drawing Sheets

MEASURING DEVICE FOR MEASURING CONSISTENCY OF CEMENT SLURRY FOR A CONSISTOMETER

TECHNICAL FIELD

This present invention relates to a device for measuring consistency of cement slurry for a consistometer.

BACKGROUND OF THE INVENTION

As for oil well cements used for cementing of shaft wall, there are extremely strict requirements on their indexes of physical and mechanical properties, such as cement thickening time. It's also explicitly formulated in National Standards for oil well cements that the cement thickening time should be tested by a pressurized consistometer.

Presently, most of the methods for measuring cement consistency for a consistometer at home and abroad are implemented according to a measuring method by the consistometer of US Chandler Engineering Company, i.e. providing a potentiometer inside a pressure vessel of a consistometer for measuring cement consistency. However, this method has the following problems:

1. Lacking high measurement accuracy. The measurement accuracy is directly affected by contact pressure of a sliding contact arm of the potentiometer, surface finish of a resistance sheet and quality of bearings. The bad conditions inside pressure vessel, such as high temperature, high pressure, high pollution and high corrosion, also cause the technical index of the potentiometer that has already been adjusted decrease quickly. A gross error is inevitably produced and an incorrect value is shown directly sometimes.

2. The potentiometer having too many wearing components requiring a regular repair and correction, which, however, is rather difficult.

These deficiencies described above limit the improvement of the technical index of the conventional potentiometer measuring method.

SUMMARY OF THE INVENTION

The object of the invention is to provide a new type of measuring device with high measurement accuracy for measuring consistency of cement slurry for a consistometer.

The measuring device according to the invention may comprise a high-pressure vessel, a slurry cup and a magnetic driver, wherein the slurry cup is rotatably mounted inside the high-pressure vessel by the magnetic driver, a plurality of stir blades are hanged in the slurry cup, and the magnetic driver is driven by a driving motor which is located outside the high-pressure vessel and is provided with a tension sensor.

The magnetic driver may further be provided with a passive internal magnet, and the driving motor may further be provided with an active external magnet which matches the passive internal magnet.

The driving motor may further comprise a stator and a rotor, wherein the active external magnet is directly mounted on the rotor.

The rotor may have a hollow structure; the active external magnet is mounted on the inner wall of the rotor.

The magnetic driver may further be coaxially nested in the active external magnet.

The magnetic driver may further comprise a driver case mounted to the bottom of the high-pressure vessel, and a magnetic-driven spindle mounted in the driver case, wherein the passive internal magnet is located at one end of the magnetic-driven spindle and the other end of the magnetic-driven spindle is secured to the bottom of the slurry cup via a driving disk.

The driving motor may further comprise a motor case and a first bearing, wherein the stator is mounted inside the motor case, the first bearing is mounted on the motor case, and the rotor is rotatably mounted on the motor case through the first bearing.

The motor case may further be rotatably hanged on and secured to the driver case through a second bearing.

The magnetic driver may further comprise a driver case mounted to the bottom of the high-pressure vessel, and a magnetic-driven spindle nested in the driver case, wherein one end of the magnetic-driven spindle is provided with the passive internal magnet and the other end of the magnetic-driven spindle is secured to the bottom of the slurry cup.

The driving motor may further comprise a motor case, a first bearing, a rotor having a hollow structure, and an active external magnet, wherein a stator is mounted inside the motor case; the first bearing is mounted on the motor case; the rotor is rotatably mounted on the motor case through the first bearing; the active external magnet is mounted to the inner wall of the rotor; the motor case is rotatably hanged on and secured to the driver case through a second bearing; when the stator drives the rotor to rotate, the rotor drives the active external magnet to rotate, thus driving the magnetic-driven spindle of the magnetic driver to rotate; and the torque from the driving motor is measured by the tension sensor, thereby measuring the consistency of cement slurry.

The advantages of the invention are described below.

1. The invention cancels the conventional mode for measuring consistency by a potentiometer. It takes use of the tension sensor to measure the torque transferred from the driving motor to the magnetic driver, i.e. the cutting torque created by the stir blades on the cement slurry within the slurry cup, thereby measuring the consistency of cement slurry and greatly enhancing the stability and measurement accuracy of the measurement system.

2. The new type of structure of the measuring device provided by the invention has less wearing components, is easy to maintain and also has simplified the operation of the consistometer.

3. Regular correction is not required.

4. The whole index of performance of the consistometer is increased.

SPECIFIC EMBODIMENTS

As described in the accompanying drawings and the following detailed discussion, one aspect of the present invention is to provide a measuring device for measuring consistency of cement slurry for a consistometer so as to greatly enhance relevant functions, such as the stability and measurement accuracy of measurement system.

The measuring device comprises a high-pressure vessel, a slurry cup and a magnetic driver, wherein the slurry cup is rotatably mounted inside the high-pressure vessel by the magnetic driver, a plurality of stir blades are hanged in the slurry cup, and the magnetic driver may be driven by a driving motor which is located outside the high-pressure vessel and is provided with a tension sensor for balancing and detecting the torque through which the driving motor drives the magnetic driver to rotate.

The magnetic driver may be directly driven by the driving motor through the cooperation between an active external magnet and a passive internal magnet, wherein the active external magnet is located in the driving motor, while the passive internal magnet is located in the magnetic driver and matched with the active external magnet. In order to accomplish this function, the driving motor may further comprise a stator and a rotor, wherein the active external magnet may be directly mounted on the rotor, and meanwhile the magnetic driver may be coaxially nested in the active external magnet. Therefore, when the stator drives the rotor to rotate, the rotor can drive the active external magnet to rotate. That is to say, the rotor is able to directly control the rotation of the active external magnet, in this way, and thereby the active external magnet controls the rotation of the magnetic driver having the passive internal magnet. The rotor may have a hollow structure, and the active external magnet is mounted to the inner wall of the rotor.

In addition, the magnetic driver may further comprise a driver case mounted to the bottom of the high-pressure vessel, and a magnetic-driven spindle nested in the driver case, wherein the passive internal magnet is located at one end of the magnetic-driven spindle and the other end of the magnetic-driven spindle may be secured to the bottom of the slurry cup by a driving disk.

The driving motor may further comprise a motor case and a first bearing, wherein the stator is mounted inside the motor case, the first bearing is mounted on the motor case, and the rotor may be rotatably mounted on the motor case through the first bearing.

The motor case may be rotatably hanged on and secured to the driver case of the magnetic driver through a second bearing. When the stator drives the rotor to rotate, the rotor drives the active external magnet to rotate. And then the magnetic-driven spindle provided with the passive internal magnet is driven to rotate by a magnetic force, thereby rotating the magnetic driver.

The embodiments of the invention will be described with reference to the accompanying drawings.

Figure 1:
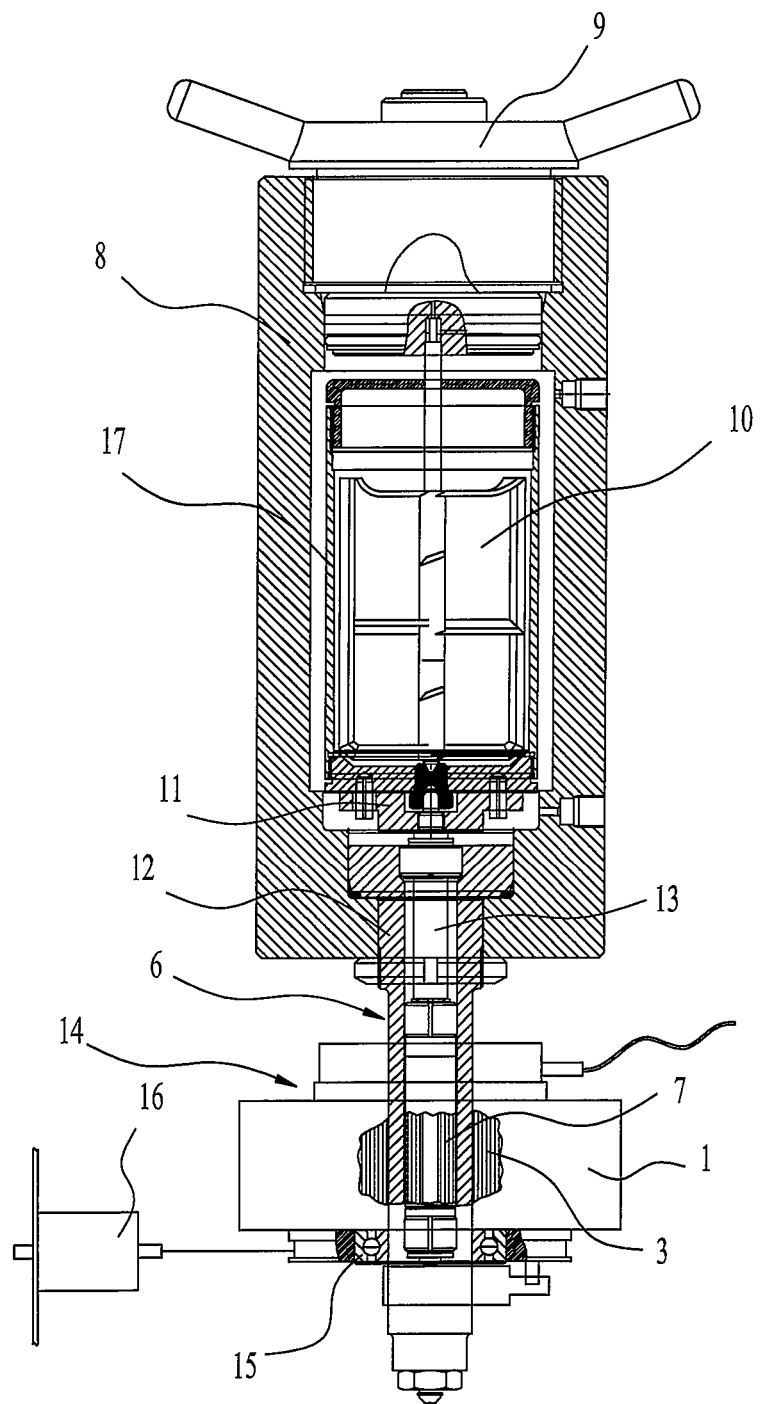
FIG. 1 illustrates the structure of the measuring device of the present invention.

As shown in FIG. 1, the measuring device according to the invention comprises a high-pressure vessel 8, a slurry cup 17 and a magnetic driver 6, wherein the slurry cup 17 is rotatably mounted inside the high-pressure vessel 8 by the magnetic driver 6, a plurality of stir blades 10 are hanged in the slurry cup 17. A shaft fixing the stir blades 10 extends out of the slurry cup 17 and is secured to a cover 9 of the high-pressure vessel 8. The magnetic driver 6 is driven by a driving motor 14 located outside the high-pressure vessel 8, the driving motor 14 is provided with a tension sensor 16 for balancing and detecting the torque through which the driving motor 14 drives the magnetic driver 6 to rotate.

As shown in FIG. 1, the magnetic driver 6 further comprises a driver case 12 mounted to the bottom of the high-pressure vessel 8 and a magnetic-driven spindle 13 nested in the driver case 12. One end of the magnetic-driven spindle 13 is provided with a passive internal magnet 7, and the other end of the magnetic-driven spindle 13 is secured to the bottom of the slurry cup 17 by a driving disk 11. The passive internal magnet 7 matches an active external magnet (described below) which is located on the driving motor 14.

Figure 2:
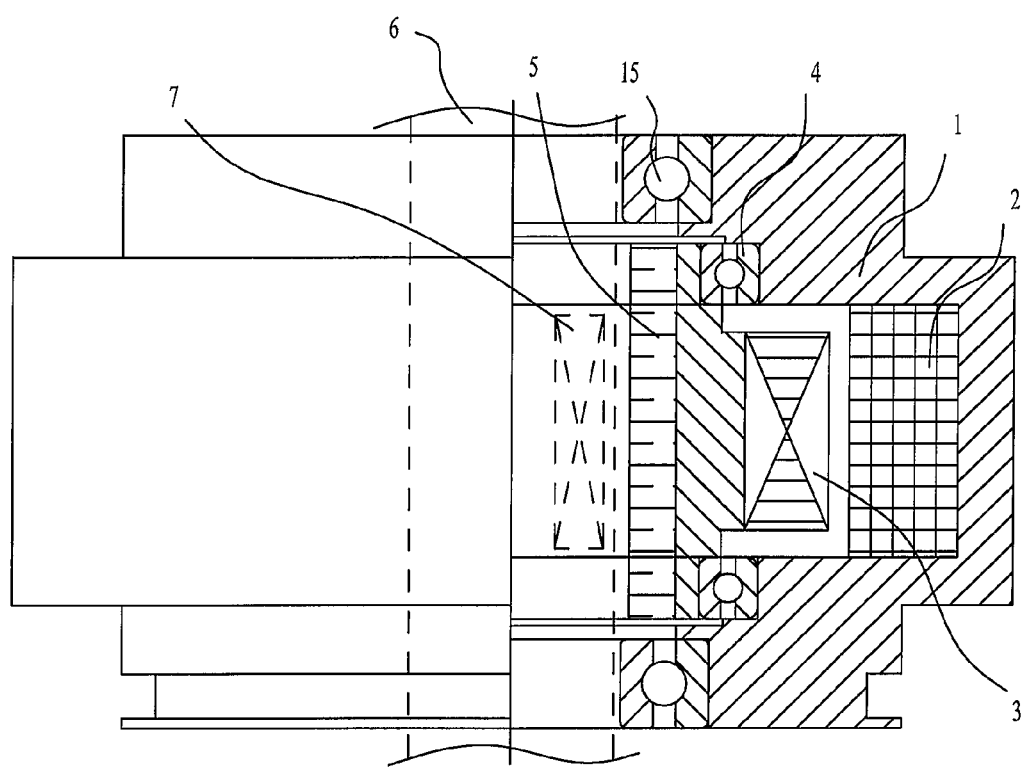
FIG. 2 illustrates the assembly structure for the driving motor and the magnetic driver according to the present invention.

As shown in FIGS. 1 and 2, the driving motor 14 further comprises a motor case 1, a first bearing 4, a rotor 3 having a hollow structure, and an active external magnet 5, wherein a stator 2 is mounted inside the motor case 1, the first bearing 4 is mounted on the motor case 1, the rotor 3 is rotatably mounted on the motor case 1 through the first bearing 4, and the active external magnet 5 is mounted to the inner wall of the rotor 3.

The motor case 1 is rotatably hanged on and secured to the driver case 12 through a second bearing 15. When the stator 2 drives the rotor 3 to rotate, the rotor 3 drives the active external magnet 5 to rotate. And then the magnetic-driven spindle 13 provided with the passive internal magnet 7 is driven to rotate by a magnetic force.

Therefore, the slurry cup 17 rotates, and the cement slurry contained within the slurry cup 17 is cut by the stir blades 10. According to the relation between an acting force and a counteracting force, the torque from the driving motor 14 can be measured by the tension sensor 16, thereby measuring the consistency of cement slurry.

The measuring device according to the invention cancels the conventional mode for measuring consistency by a potentiometer and greatly simplifies the whole measuring structure, which not only facilitates maintenance but also simplifies the operation.

In addition, since the magnetic driver is directly driven to rotate by the driving motor and the torque is measured by the tension sensor, the measurement accuracy can be greatly increased.

Besides, since the driving motor provided with the tension sensor is provided outside the high-pressure vessel, it will not be affected by the high temperature and high pressure in the high-pressure vessel, thus greatly improving the stability of measurement.

Moreover, the active external magnet 5 is directly mounted on the rotor 3, in which way the conventional power-output shaft of the rotor 3 is cancelled; meanwhile, the magnetic driver 6 having the passive internal magnet 7 which is matched with the active external magnet 5 is coaxially nested in the active external magnet 5, which minimizes the space for installation of the driving without any additional length and greatly reduces the whole volume of the consistometer, such that the consistometer can be portable. In addition, since the active external magnet 5 is directly controlled by the rotor 3, and then the magnetic driver 6 is driven to rotate by the active external magnet 5, the mechanical loss is reduced to the minimum level, which is almost zero.

What we claimed is:

1. A measuring device for measuring consistency of cement slurry for a consistometer, characterized in that said measuring device comprises:
   a high-pressure vessel,
   a slurry cup, and
   a magnetic driver, wherein
   the slurry cup is rotatably mounted inside the high-pressure vessel by the magnetic driver,
   stir blades are hanged in the slurry cup, and
   the magnetic driver is driven by a driving motor, the driving motor is located outside the high-pressure vessel, and
   a tension sensor directly connected to the driving motor to balance and detect the torque through which the driving motor drives the magnetic driver to rotate.

2. The measuring device of claim 1, characterized in that the magnetic driver is provided with a passive internal magnet, and the driving motor is provided with an active external magnet which matches the passive internal magnet.

3. The measuring device of claim 2, characterized in that the driving motor further comprises a stator and a rotor, wherein the active external magnet is directly mounted on the rotor.

4. The measuring device of claim 3, characterized in that the rotor is of a hollow structure and the active external magnet is mounted to an inner wall of the rotor.

5. The measuring device of claim 3, characterized in that the magnetic driver is coaxially nested inside the active external magnet.

6. The measuring device of claim 5, characterized in that the magnetic driver further comprises a driver case which is mounted to the bottom of the high-pressure vessel, and a magnetic-driven spindle which is nested in the driver case, wherein the passive internal magnet is located at one end of the magnetic-driven spindle and the other end of the magnetic-driven spindle is secured to the bottom of the slurry cup by a driving disk.

7. The measuring device of claim 6, characterized in that the driving motor further comprises a motor case and a first bearing, wherein the stator is mounted inside the motor case, the first bearing is mounted on the motor case, and the rotor is rotatably mounted on the motor case through the first bearing.

8. The measuring device of claim 7, characterized in that the motor case is rotatably hanged on and secured to the driver case through a second bearing.

9. The measuring device of claim 1, characterized in that the magnetic driver further comprises a driver case which is mounted to the bottom of the high-pressure vessel, and a magnetic-driven spindle which is nested in the driver case, wherein one end of the magnetic-driven spindle is provided with the passive internal magnet and the other end of the magnetic-driven spindle is secured to the bottom of the slurry cup.

10. The measuring device of claim 9, characterized in that the driving motor further comprises a motor case, a first bearing, a rotor having a hollow structure, and an active external magnet, wherein a stator is mounted inside the motor case, the first bearing is mounted on the motor case, the rotor is rotatably mounted on the motor case through the first bearing, the active external magnet is mounted to an inner wall of the rotor, and the motor case is rotatably hanged on and secured to the driver case through a second bearing, when the stator drives the rotor to rotate, the rotor drives the active external magnet to rotate, thus driving the magnetic-driven spindle of the magnetic driver to rotate, and the torque from the driving motor is measured by the tension sensor, thereby measuring the consistency of the cement slurry.

11. The measuring device of claim 10, characterized in that a shaft fixing the stir blades extends out of the slurry cup and is secured to a cover of the high-pressure vessel.

12. The measuring device of claim 1, characterized in that the tension sensor is located outside of the high-pressure vessel.

13. The measuring device of claim 1, characterized in that a shaft fixing the stir blades extends out of the slurry cup and is secured to a cover of the high-pressure vessel.

14. A measuring device for measuring consistency of cement slurry for a consistometer, characterized in that said measuring device comprises:
 a high-pressure vessel;
 a slurry cup;
 a magnetic driver; and
 a tension sensor, wherein
 the slurry cup is rotatably mounted inside the high-pressure vessel by the magnetic driver,
 stir blades are hanged in the slurry cup,
 a shaft fixing the stir blades extends out of the slurry cup and is secured to a cover of the high-pressure vessel,
 the magnetic driver is driven by a driving motor that is located outside the high-pressure vessel, and
 the tension sensor is located outside of the high-pressure vessel and is directly connected with the driving motor to balance and detect the torque through which the driving motor drives the magnetic driver to rotate.

* * * * *